(12) United States Patent
Williams et al.

(10) Patent No.: US 7,092,764 B2
(45) Date of Patent: Aug. 15, 2006

(54) HELIX ROTATION BY TRACTION

(75) Inventors: Terrell M. Williams, Brooklyn Park, MN (US); Laurie D. Foerster, Mound, MN (US); Bruce E. Chivers, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 666 days.

(21) Appl. No.: 10/136,792

(22) Filed: Apr. 30, 2002

(65) Prior Publication Data

US 2002/0177888 A1 Nov. 28, 2002

Related U.S. Application Data

(63) Continuation-in-part of application No. 09/559,161, filed on Apr. 26, 2000, now Pat. No. 6,516,230.

(51) Int. Cl.
*A61N 1/00* (2006.01)

(52) U.S. Cl. ..................................... 607/115

(58) Field of Classification Search ........ 607/115–133; 132/210; 604/264, 127; 87/36; 600/372–382; 192/209; 84/397; 57/214; 174/69
See application file for complete search history.

(56) References Cited

U.S. PATENT DOCUMENTS

| 2,456,015 | A | * | 12/1948 | Orser | 174/69 |
|---|---|---|---|---|---|
| 3,572,344 | A | | 3/1971 | Bolduc | 128/418 |
| 3,610,084 | A | * | 10/1971 | Behringer | 84/397 |
| 3,705,489 | A | * | 12/1972 | Smollinger | 57/214 |
| 3,844,292 | A | | 10/1974 | Bolduc | 128/418 |
| 3,902,501 | A | | 9/1975 | Citron et al. | 128/418 |
| 4,135,518 | A | * | 1/1979 | Dutcher | 600/374 |
| 4,161,952 | A | | 7/1979 | Kinney et al. | 128/786 |
| 4,506,680 | A | | 3/1985 | Stokes | 128/786 |
| 4,572,344 | A | * | 2/1986 | Horiuchi et al. | 192/209 |
| 4,951,687 | A | | 8/1990 | Ufford et al. | 128/786 |
| 4,975,543 | A | * | 12/1990 | Saunders | 174/369 |
| 4,988,347 | A | | 1/1991 | Goode et al. | 606/1 |
| 5,056,516 | A | | 10/1991 | Spehr | 128/419 P |
| 5,217,028 | A | * | 6/1993 | Dutcher et al. | 607/120 |
| 5,231,996 | A | | 8/1993 | Bardy et al. | 128/785 |
| 5,246,014 | A | | 9/1993 | Williams et al. | 607/122 |

(Continued)

FOREIGN PATENT DOCUMENTS

WO    WO 01/80941 A2    11/2001

*Primary Examiner*—George Manuel
(74) *Attorney, Agent, or Firm*—Girma Wolde-Michael; Paul H. McDowall

(57) ABSTRACT

The present invention includes a "Z shaped" configuration for a pair of internal windings of a fiber core of a medical electrical lead which can be configured as or windings to provide counter-rotation an implanted cardiac lead. When fully assembled and implanted within a patient, a screw-type active fixation electrode, such as a helical electrode, electrically couples to a coil conductor and mechanically couples to a loop formed at an end of the Z-shaped braided fiber. To remove the lead, an axial traction force is applied and as the Z-shaped braids begin to unwind rotational forces operate to unscrew the helical electrode. A lead constructed according to the present invention rotates counterclockwise and thus essentially unscrews the active fixation electrode.

20 Claims, 3 Drawing Sheets

U.S. PATENT DOCUMENTS

| | | | |
|---|---|---|---|
| 5,584,873 A | 12/1996 | Shoberg et al. | 607/122 |
| 5,760,341 A | 6/1998 | Laske et al. | 174/126.2 |
| 5,796,044 A | 8/1998 | Cobian et al. | 174/103 |
| 5,837,007 A * | 11/1998 | Altman et al. | 607/127 |
| 5,851,226 A | 12/1998 | Skubitz et al. | 607/126 |
| 5,871,532 A | 2/1999 | Schroeppel | 607/128 |
| 5,897,584 A * | 4/1999 | Herman | 607/122 |
| 5,935,159 A | 8/1999 | Cross, Jr. et al. | 607/116 |
| 5,971,967 A * | 10/1999 | Willard | 604/264 |
| 6,032,063 A | 2/2000 | Hoar et al. | 600/372 |
| 6,052,625 A | 4/2000 | Marshall | 607/122 |

\* cited by examiner

# HELIX ROTATION BY TRACTION

CROSS-REFERENCE TO RELATED APPLICATION

This Application is a continuation-in-part of U.S. patent application Ser. No. 09/559,161, filed Apr. 26, 2000 now U.S. Pat. No. 6,516,230, and entitled "Medical Electrical Lead with Fiber Core," the contents of which are hereby incorporated herein.

FIELD OF THE INVENTION

The present invention relates to a method for removal of an implanted lead from a patient's body and specifically for removal of transvenous endocardial leads from a patient's heart and the venous paths thereto.

BACKGROUND OF THE INVENTION

Generally speaking, a pacing lead permits an implantable medical device (IMD) such as an implantable pulse generator (IPG) or other IMD to sense the activity of the heart and to provide electrical stimulation to the heart. Pacing leads can be either epicardial (e.g., attached to the exterior surface of the heart), or endocardial (e.g., attached to an interior location of the heart). Endocardial leads are normally placed into contact with the endocardial tissue by passage through the venous system, such as through the subclavian vein or other easily accessible veins located near the implant site of the IMD. Thus a transvenous, endocardial lead refers to a pacing lead that contacts cardiac endocardial tissue through a vein.

An endocardial lead is in electrical communication with the heart via an electrode at its distal end and thereby provides an electrical pathway between the IPG and endocardial tissue. Using this electrical pathway, the IPG is able to both pace the heart via electrical impulses and sense cardiac depolarizations.

In the past, various types of transvenous endocardial leads have been introduced into different chambers of the heart including the right ventricle, right atrial appendage and atrium as well as the coronary sinus. These leads usually are composed of an insulator sleeve that contains a coiled conductor having an electrode tip attached at the distal end. The electrode tip is held in place within the trabeculations of endocardial tissue. The distal ends of many available leads include passive fixation designs that may consist of flexible tines, wedges, or finger-like projections that extend radially outward and usually are molded from and integral with the insulator sleeve of the lead. These tines allow better containment by the trabeculations of endocardial tissue and help prevent dislodgement of the lead tip. Active fixation leads, on the other hand, are designed with lead tips that are lodged into the myocardium and may consist of helical coils, small sharp tips, and barbed tines among others.

Once an endocardial lead is implanted within a chamber of the heart, the body's reaction to its presence furthers its fixation within the heart. Specifically, shortly after implant, a blood clot forms about the lead tip due to enzymes released in response to the irritation of the endocardial tissue caused by the electrode tip which can be any one of a plurality of designs, tined, helical, flanged, among others. Over time, fibrous scar tissue eventually forms over the distal end. This scarring usually occurs within three to six months of implantation. In addition, fibrous scar tissue often forms, in part, over the lead's body or insulative sleeve within the vein through which the lead was passed.

Although the state of the art in pacemaker and lead technology has advanced considerably, endocardial leads nevertheless occasionally fail, due to a variety of reasons, including insulation breaks, breakage of the inner helical coil conductor thereof and an increase in electrode resistance. Also, in some instances, it may be desirable to stimulate different portions of the heart than those being stimulated with leads already in place. Due to these and other factors, therefore, a considerable number of patients may come to eventually have more than one, and sometimes as many as four or five, abandoned, unused leads in their venous system and heart.

Abandoned transvenous leads increase the risk that medical complications will develop. Possible complications associated with leaving unused leads in the heart and venous system include an increased likelihood that such a lead may become a site of infection. Development of an infection may, in turn, lead to septicemia, a possibly fatal complication. Unused leads may also cause endocarditis. Furthermore, unused leads may entangle over time, thereby increasing the likelihood of blood clot formation. Such clots may embolize to the lung and produce severe complications or even death. The presence of unused leads in the venous pathway and inside the heart can also cause considerable difficulty in the positioning and attachment of new endocardial leads in the heart. Moreover, multiple leads within a vein may impede blood flow or occlude the blood vessel, causing swelling of the arm.

As serious as the risks associated with leaving an unused lead in place may be, the risks associated with past methods and devices for lead removal were often greater. One technique used to remove a lead was the application of traction and rotation to the outer free end of the lead. This technique, however, could only be done before the lead tip became fixed in scar tissues within the trabeculations of cardiac tissue, such as at the apex of the right ventricle. Since it is very difficult to determine the formation of a clot, even shortly after lead implantation, there exists the risk a clot has already formed. Removal of a lead at that time may cause various sized emboli to pass to the lungs, thereby producing severe complications.

In cases where the lead tip has become attached by fibrous scar tissue to the heart wall, removal of the lead has presented further major problems and risks. Porous lead tips may have an ingrowth of fibrous scar tissue attaching them to the heart wall. Sufficient traction on such leads in a removal attempt could cause disruption of the wall prior to release of the affixed lead tip, causing fatality. Moreover, a sheath of fibrotic scar tissue may further prevent lead removal and endothelium surrounding the outer surface of the lead body and specifically the insulator sleeve, as mentioned above, at least partway along the venous pathway. Such "channel scar" tissue prevents withdrawal because of encasement of the lead. Continual strong pulling or twisting of the proximal free end of the lead could cause rupturing of the right atrial wall or right ventricular wall. Encasement by fibrous scar tissue in the venous pathway and in the trabeculations of cardiac tissue typically occurs within three to six months after the initial placement of the lead.

In the context of implantable leads, and particularly in the context of implantable cardiac leads, there is often a need to remove a lead after it has been implanted in a patient's body for some period of time. In conjunction with lead removal, it is often necessary to apply traction to the lead, in order to pull it free from tissue adhering thereto. It has therefore been recognized for some time that a reinforcement of some type, extending along the lead body would be beneficial, in order to prevent breakage or partial disassembly of the lead during removal. For example, in U.S. Pat. No. 5,231,996 issued to Bardy et al., a variety of reinforcement mechanisms are disclosed, including cords, filaments, braids, and the like.

More recently, in the context of implantable cardiac leads, the use of cabled or stranded conductors in place of the previously more commonly employed coiled conductors has become more popular. These cabled or stranded conductors, such as disclosed in U.S. Pat. No. 5,584,873 issued to Shoberg et al., U.S. Pat. No. 5,760,341 issued to Laske et al. and U.S. Pat. No. 5,246,014 issued to Williams et al. inherently provide an increased tensile strength lead, at least along the segment between the point at which the stranded or cabled conductor is coupled to an electrode and the point at which the conductor is coupled to an electrical connector at the proximal end of the lead. While this new conductor inherently provides a lead of enhanced tensile strength, in most endocardial cardiac pacing leads employing cabled or stranded conductors, the conductor that extends to the distal-most portion of the lead is still a coiled conductor in order to permit passage of a stylet. This distal-most portion of the lead is the portion of the lead that is most likely to be firmly embedded in fibrous tissue. It is therefore desirable that this portion of the lead in particular should be capable of withstanding high tensile forces without breakage.

As the designs of pacing leads have progressed over the years, there has been a general trend toward reduction in the diameter of the bodies of such leads, that is, those that are $\leq 4$ French in diameter. However, as the diameter of the lead body is reduced, the production of a pacing lead that has an adequate tensile strength to allow relatively easy extraction via traction and rotation has become more difficult.

One approach to providing a small diameter lead with a high tensile strength is to fabricate the lead using an inextendible conductor, for example, a stranded conductor as disclosed in U.S. Pat. No. 5,246,014 issued to Williams et al., a cabled conductor as disclosed in U.S. Pat. No. 5,584, 873 issued to Shoberg et al., or a tinsel-wire conductor as disclosed in U.S. Pat. No. 3,844,292 issued to Bolduc all incorporated herein by reference in their entireties. Another approach to increasing the tensile strength of a lead including a coiled, normally extensible conductor is to provide a reinforcing fiber or core within the lead, as disclosed in the previously mentioned U.S. Pat. No. 5,231,996 issued to Bardy et al., and U.S. Pat. No. 5,056,516, both also incorporated herein by reference in their entireties.

The previously referenced U.S. patent application Ser. No. 09/559,161, entitled, "Medical Electrical Leads with Fiber Core," which discloses how to fabricate a high strength, small diameter pacing lead. This lead that can be as small as 2 to 4 French in diameter utilizes a fiber core fabricated from a single length of fiber that is d-oubled and twisted together, around which a multi-filar coil is wound. The composite conductor coil/core structure is coupled to a connector assembly at its proximal end and, preferably, to a helical electrode at its distal end. Having such a pacing lead available, there still remains the issue of how to extract such a lead in those patients who require such a procedure.

SUMMARY OF THE INVENTION

The present invention is directed toward the easy removal of an implantable medical electrical lead such as that disclosed in the parent case previously referenced and incorporated herein. This lead incorporates a helical electrode, connected to a helical coiled conductor that is wound around a twisted fiber core. The fiber core of the parent application consists of a doubled over, length of fiber cord twisted with "S-shaped" windings during fabrication. The inventors hereof have discovered that the manner in which the fiber core is wound is vital to the ultimate result, that is, the extraction of the electrode tip coupled to the lead. In particular, the present invention is directed to a medical electrical lead having a series of Z-shaped braids in the doubled over, length of fiber cord. The composite coil/core structure is coupled to a connector assembly at its proximal end and a helical electrode at its distal end. Other electrode(s) may also be used so that the lead may be used for unipolar, bipolar, or multipolar pacing and sensing.

In a preferred embodiment of the invention, the lead may be removed by counter-rotation of the helical tip as traction is applied to the lead. As traction is applied to the lead, the twisted fibers begin to unwind and lose their "Z-shape." In the process, the helical tip counter-rotates and comes free of the tissue. The electrode tip is the only portion of the lead that rotates. The traction force tends to extend the lead body (i.e., the lead's insulation and the coil), which causes the Z-shaped braid twisted into the fiber core to be relieved. The resulting torque is transferred to the electrode tip of the lead. Of course, the medical electrical lead of the present invention is intended to impart counterclockwise rotation when tensile force is applied to the lead body. In the event that reverse-direction threads were present on an electrode, or clockwise rotation was desired, the Z-shaped braid would simply need to be reversed.

Because the lead is isodiametric, there is no need to insert a sheath over the lead to cut any fibrotic tissue that may have build up around the lead or a bulge found at distal ends of other non-isodiametric leads. Moreover, with a small diameter of a nominal 2.6 French lead, scar tissue within the vein forms a thin, lubricious sheath within which the lead can slide out when traction is applied after release of the lead tip. These facts have been verified in an extraction study of up to five years in animal studies.

Although the present invention is described in terms of the use of a helical coil at the end of a small diameter isodiameteric lead, the same or similar type of lead may also be used as an epicardial/myocardial lead. When coupled with newer implant techniques and devices, such a lead when applied epicardially, may prove very efficacious when used with young children.

DETAILED DESCRIPTION OF THE DRAWINGS

Figure 1:
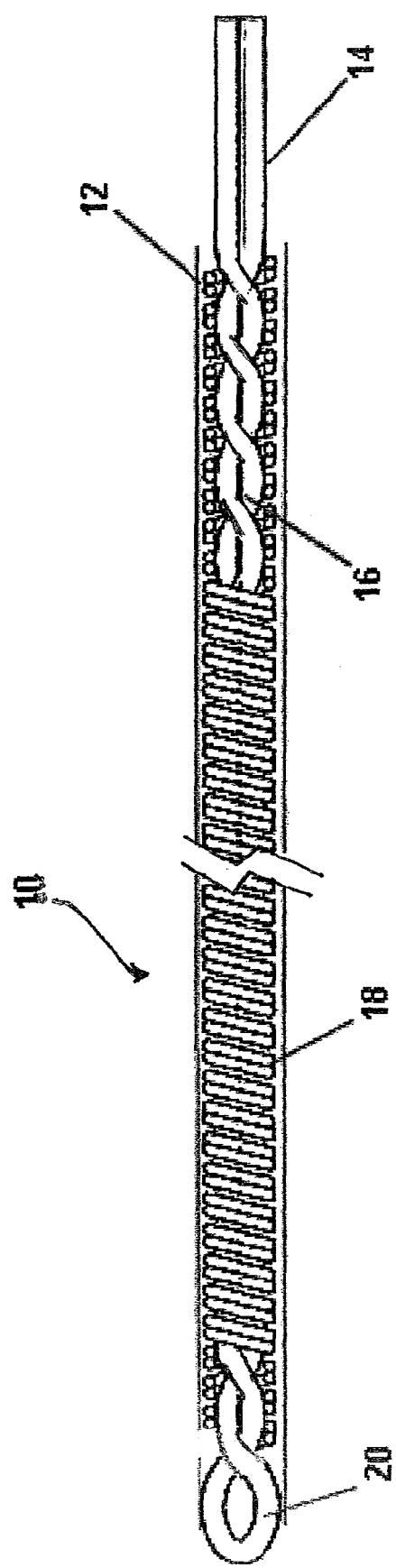
FIG. 1 is a side, cut-away view of the distal and proximal portions of the lead without the screw-in electrode attached.

In the side, cut-away view of lead 10 in FIG. 1, the important elements of a small diameter fiber core lead are displayed. Insulative cover 12 surrounds internal coil conductor 18 that, in turn, surrounds wound fiber 14. Dual strand fiber core 14 extends the length of the lead 10. The lead 10 is essentially isodiameteric along its length such that all the elements generally have the same diameter.

Also illustrated is the "Z-shaped" configuration of the windings 16 of the fiber core 14 which, as will be illustrated and described herein, are a primary source of counter-rotation of an electrode (not shown) coupled to cardiac tissue (not shown) during extraction of lead 10. When fully assembled and implanted within a patient, an electrode (e.g., electrode 22 of FIG. 2) is electrically coupled to the coil conductor 18 and is mechanically coupled to the loop 20 of the Z-shaped twisted fiber 14. While the illustrated and described embodiment depicts and refers to a "Z-shape" to the windings 16, no such limitation should be found or implied with respect to the present invention. Other configurations may be used in place of the "Z-shape" depicted and described. For example, any similar mechanical interlocking mechanism that offers overall resiliency and enough flexibility to promote efficient insertion and which produces a rotational force in response to axial tensile forces applied to the lead may substitute for the configuration described and depicted herein. An example of such a configuration includes a saw tooth-like shape, and the like.

In addition, while not described or depicted in this disclosure, the fiber core 14 may be coated with a friction reducing material to promote the unwinding of the fiber 14 in response to applied tensile force. Furthermore, with respect to the fiber core 14 other materials may be used such as a resilient polymer material, natural or synthetic material, cords, and the like.

Figure 2:
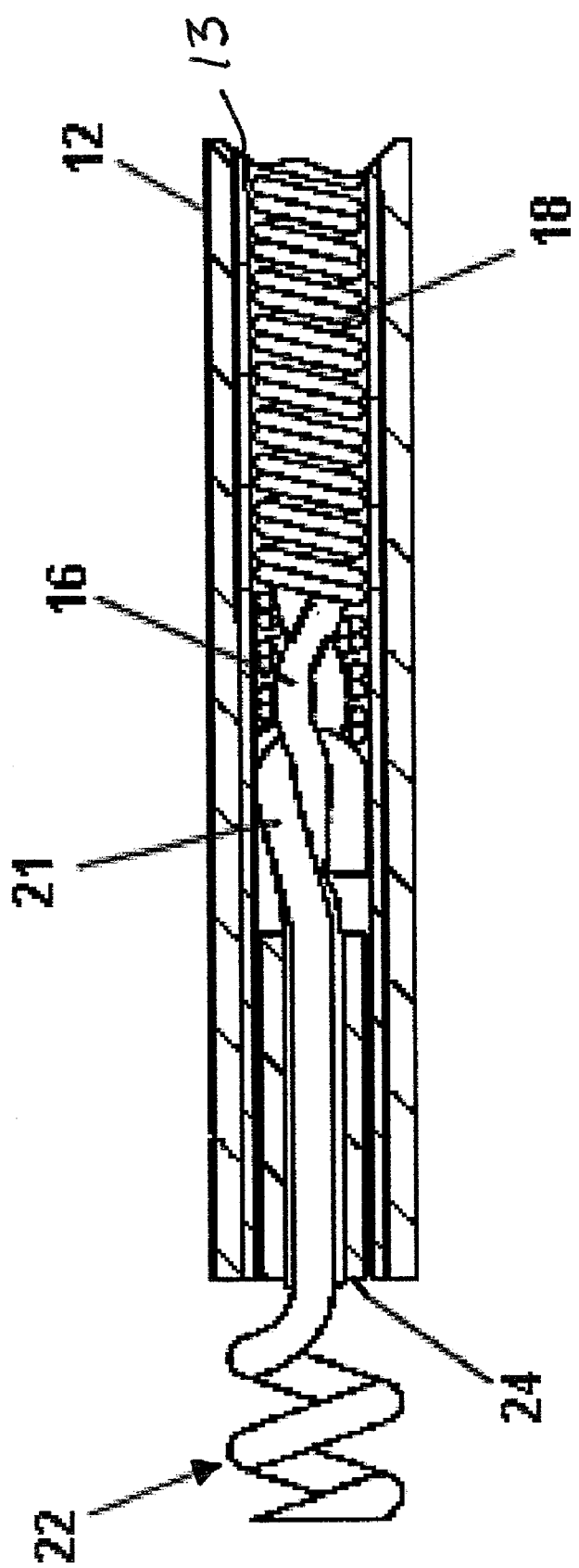
FIG. 2 is a side, cut-away view of the distal portion of the lead with a helical electrode attached.

As depicted in FIG. 2, a helical-type electrode 22 is the preferred electrode for used in conjunction with the present invention. Of course, the lead 10 may be a multi-polar type lead or a unipolar type lead.

A single cord 14 of approximately twice the desired length is preferably used to produce the fiber core 14. The cord 14 is folded in half and then twisted to produce the "Z-shaped" windings 16 (and a loop 20 is preferably formed with a portion of the folded cord 14—at the distal end). In one embodiment of the present invention, 100 Z-shaped windings were equally distributed over a 53.5 inch length of the lead 10. The resulting lead assembly created according to the present invention is isodiametric. That is, the lead has essentially the same diameter throughout its length, which the inventors believe is an additional advantage of the present invention and perhaps even vital to providing reliable extraction of the lead. In addition, the lead 10 is preferably also very compact. A lead 10 constructed according to the present invention has an outer diameter of preferably less than 4 French (and more preferably, approximately 2 to 2.6 French in outer diameter).

Generally, in most prior art leads the distal ends of a given lead includes some protrusion at the distal end, stemming from the attachment of the electrode tip to the lead body. This protrusion almost immediately fosters fibrotic tissue buildup. The isodiametric design of leads according to the present invention, however, tends to minimize the buildup of fibrotic tissue, since there is little to no additional structure, junction or protrusion to which such tissue can readily attach. The extremely small diameter of the lead itself, while it does not totally eliminate fibrosis, tends to build a specific type of fibrotic tissue around itself. A lubricious tube/sheath typically slowly builds up. Because the interior of this tube is so slippery, a small diameter lead of the present invention has been found to be easily extracted without any other implements being used during the extraction process, especially since there are no protrusions at or near the lead tip.

Referring to FIG. 1 and FIG. 2, outer insulative sheath 12 is illustrated. The outer insulation 12 is preferably fabricated of a non-conducting biocompatible polymer such as silicone rubber, polyurethane and the like. Preferably, the outer sheath 12 surrounds an inner liner (liner 13 as shown in FIG. 2) also constructed of biocompatible polymer (which may be the same or different from the material used to construct sheath 12). These two layers of insulation 12,13 may be applied over a composite coil/core structure to produce lead 10 with an outer diameter of less than 4 French (preferably less than about 3 French), and, in one specific embodiment envisioned in the present invention, a lead 10 having an outer diameter of approximately 2 French.

Referring again to FIG. 2, is a sectional view of the distal portion of the lead 10 illustrated in FIG. 1, though now with a helical electrode 22 attached. In this view, loop 20 formed at the distal end of fiber core 14 is connected to a corresponding loop 21 at the proximal end of helical electrode 22. This type of construction serves to mechanically interconnect the electrode to coil conductor 18. Electrical connection is then established therebetween (e.g., by soldering, welding, crimping ends of conductor coil 18 to a part of helical electrode 22 and the like). In an alternative embodiment not illustrated in the drawings, electrical connection may be accomplished by welding the ends of conductor coil to a portion of the helical electrode 22. The resultant increase in tensile strength is also a benefit in conjunction with the extraction of the lead 10, if required. Cylindrical outer metal sleeve 24 serves to prevent intrusion of body fluids when the tip is sealed with adhesive, as well to provide a generally rigid electrode head assembly that facilitates rotation of helical electrode 22 during implantation of the lead 10, when the entire lead is placed under traction. On the other hand, when extraction of the lead 10 is taking place, the Z-shaped braid 16 of the fiber core 14 begins to unwind and thereby impart rotational force to the helical electrode 22. That is, when a continuous tensile force is applied to a proximal portion of the lead 10, the tensile force is converted to a rotational force based on the direction in which the Z-shaped braids were originally wound (or twisted). Of course, the Z-shaped braid inherently provides a unidirectional rotational force (i.e., a force only in a single direction) which, according to the present invention, is a force promoting a counterclockwise rotation of the lead 10.

Figure 3:
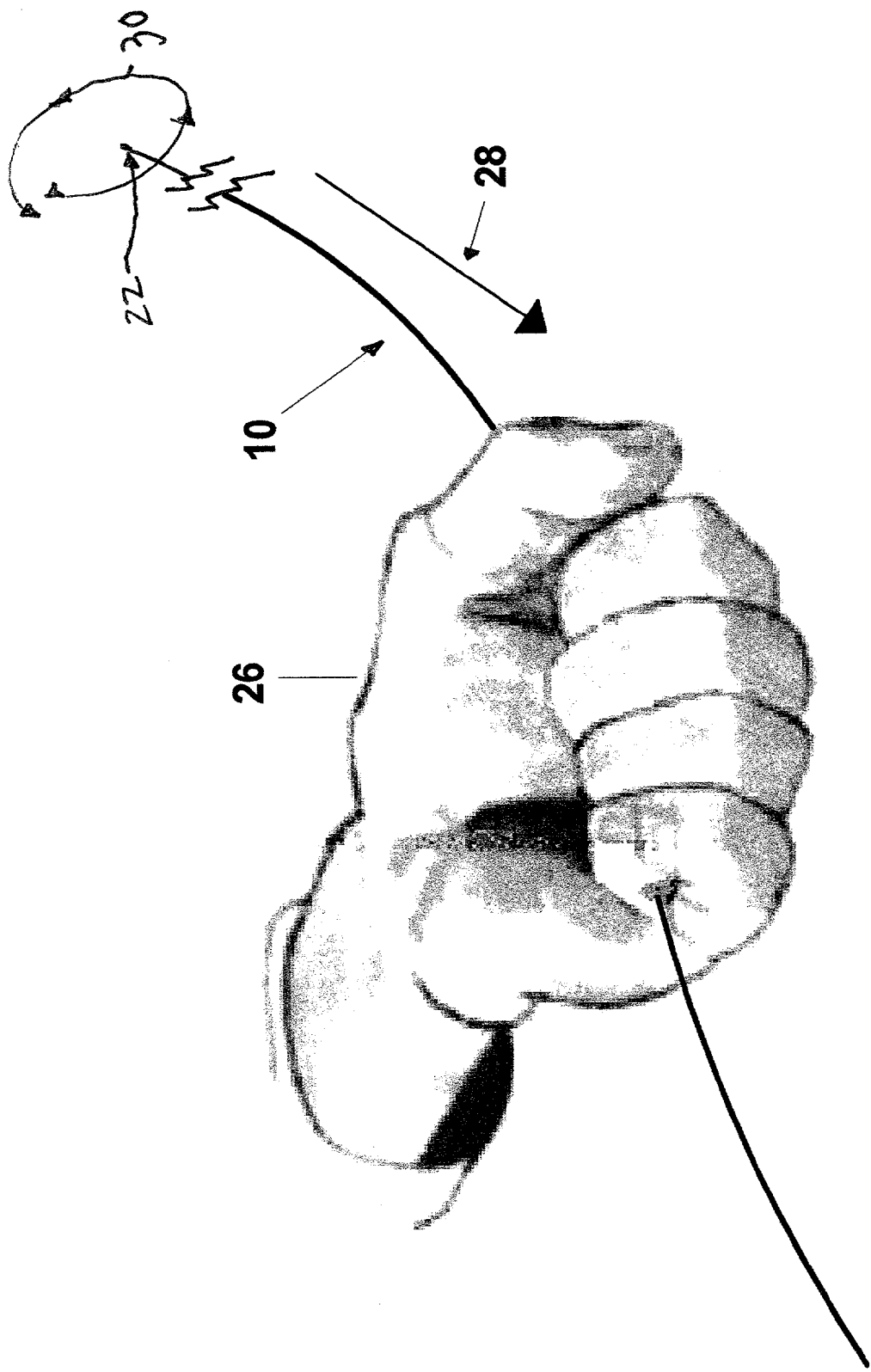
FIG. 3 is a schematic view of the lead with traction being manually applied to the proximal end of the lead by the physician.

FIG. 3 illustrates one method of traction that may be applied to the lead 10 illustrated in FIG. 1 of the present invention. Preceding the application of traction and not illustrated are other procedures performed by the physician as is known and used in the art. The IMD pocket is cut open and the proximal end of the lead is detached from the IMD. If the lead has been wound around the IMD during implant, the fibrotic tissue must be cut away from the lead. Thereafter, sutures that may have been used to secure the lead at the entry point to the vein must be severed, etc.

At this point, the physician may firmly grasp 26 lead 10 and gently pull in direction indicated (arrow 28). At a traction force threshold, the essentially linear traction force applied will tend to begin to unwind the Z-shaped braid of the fiber core 14 which creates rotation to the lead 10 (arrow 30). As described, the rotation is counterclockwise rotation which tends to reverse, or unscrew, the helical electrode 22 out of the cardiac tissue. When the electrode 22 is free of the cardiac tissue, the portion of the lead 10 remaining in the body may be pulled through the lubricious, uniform diameter fibrotic sheath for complete removal of the lead 10.

The preceding specific embodiments are illustrative of the practice of the invention. It is to be understood, therefore, that other expedients known to those of skill in the art or disclosed herein may be employed without departing from the invention or the scope of the appended claims. It is therefore to be understood that the invention may be practiced otherwise than is specifically described, without departing from the scope of the present invention. As to every element, it may be replaced by any one of infinite equivalent alternatives, only some of which are disclosed in the specification.

We claim:

1. A medical electrical lead, comprising:
   an elongated insulative sheath having proximal and distal ends;
   first and second electrical components, located such that a length of said insulative sheath extends therebetween; and
   a coil/core structure mechanically and electrically coupling said first and second electrical components disposed within said insulative sheath, said coil/core structure comprising a fiber core twisted in a Z-shape braid and having an elongated electrical conductor wound around the fiber core,
   wherein the elongated electrical conductor is coupled electrically to the first and second electrical components, and the fiber core is mechanically coupled to the first and second electrical components so that when a tensile force is applied between the first and second electrical components the Z-shape braid of the fiber core untwists thus imparting counter-rotational motion to the first electrical component.

2. The lead of claim 1, wherein the fiber core comprises two lengths of a single fiber cord, folded back upon itself to define a loop at one end thereof.

3. The lead of claim 1, wherein the elongated electrical conductor applies compressive force to the fiber core.

4. The lead of claim 1, wherein the first electrical component is a helical electrode.

5. The lead of claim 1, wherein the second electrical component is an electrically conductive pad.

6. The lead of claim 1, wherein the medical electrical lead is a bipolar lead.

7. The lead of claim 1, wherein the coiled conductor is wound around the first electrical component.

8. The lead of claim 1, wherein the lead has a diameter of about 2.6 French.

9. The lead of claim 1, wherein at least a portion of the lead adjacent the first electrical component is isodiametric.

10. The lead of claim 1, wherein the insulative sheath is formed of a biocompatible polymer.

11. The lead of claim 10, wherein the elongated insulative sheath is an outer sheath and further comprising an inner insulative sheath disposed between the outer sheath and the coil/core structure.

12. The lead of claim 11, wherein the lead has an outer diameter less than about 4 French.

13. The lead of claim 12, further comprising a cylindrical sleeve member disposed around a shaft portion of the first electrical component and at least partially covered by the outer sheath and the inner sheath.

14. A method of constructing a medical electrical lead, comprising the steps of:
   producing a coil/core structure by twisting two segments of fiber cord around one another to produce a fiber core having a Z-shaped braid and winding an elongated electrical conductor around the fiber core;
   electrically coupling opposite ends of the elongate electrical conductor to a first and a second electrical component;
   mechanically coupling opposite ends of the fiber core to the first and second electrical components so that the twisted segment provides a rotation during axial tension between said first and second components; and
   encasing substantially all the coil/core structure with an insulative sheath.

15. The method of claim 14, wherein producing the coil/core structure comprises the steps of: folding a fiber cord back upon itself to define the two segments of fiber cord and thereby providing a loop of fiber cord at one end thereof.

16. The method of claim 15, wherein electrically coupling the metal conductor to the first electrical component comprises winding the metal conductor around the first electrical component.

17. The method of claim 14, wherein the encasing step is followed by an additional encasing step wherein The encased lead is encased in a second insulative sheath thereby constructing a double-sheathed lead.

18. A medical electrical lead, comprising:
   an elongated non-conductive resilient cord segment, folded over and twisted to form a series of Z-shaped braids and having a loop formed at a distal end;
   an elongated electrical conductor helically wrapped around a majority of the elongated resilient cord to thereby constrain the Z-shaped braids and not constrain the loop;
   an electrode electrically coupled to the distal end portion of the elongated electrical conductor and mechanically coupled to the loop of the elongated non-conductive resilient cord so that the braids rotate upon axial tension applied to said cord; and
   an insulative sheath surrounding substantially all of the medical electrical lead with the exception of at least a portion of the electrode.

19. The medical electrical lead of claim 18, wherein the lead has a lead diameter less than about 4 French.

20. The medical electrical lead of claim 18, further comprising an additional insulative sheath covering a majority of the surface of the insulative sheath.

* * * * *

UNITED STATES PATENT AND TRADEMARK OFFICE
CERTIFICATE OF CORRECTION

PATENT NO. : 7,092,764 B2
APPLICATION NO. : 10/136792
DATED : August 15, 2006
INVENTOR(S) : Williams et al.

Page 1 of 1

It is certified that error appears in the above-identified patent and that said Letters Patent is hereby corrected as shown below:

On the title page item (57), in the abstract, line 3, delete "...configured as or windings..." and insert --...configured as z-shaped braids or windings...--

On the title page item (57), in the abstract, line 4, delete "...counter-rotation an..." and insert --...counter-rotation to an...--

Signed and Sealed this

Third Day of April, 2007

JON W. DUDAS
*Director of the United States Patent and Trademark Office*